United States Patent [19]

Kramer

[11] Patent Number: 4,566,455

[45] Date of Patent: Jan. 28, 1986

[54] SKIN TEMPERATURE CONTROL

[75] Inventor: Robert W. Kramer, League City, Tex.

[73] Assignee: H. Mervin Hughes, II, Houston, Tex.

[21] Appl. No.: 593,861

[22] Filed: Mar. 27, 1984

[51] Int. Cl.$^4$ ............................................. A61F 7/02
[52] U.S. Cl. ................................ 128/380; 2/171.2; 62/259.3; 128/400
[58] Field of Search ............. 128/400, 402, 403, 380; 2/413, 420, 171.2; 34/99; 165/46; 62/259.3

[56] References Cited

U.S. PATENT DOCUMENTS

| | | | |
|---|---|---|---|
| 301,931 | 7/1884 | Smith et al. | 128/402 X |
| 1,894,709 | 1/1933 | Salm | 34/99 |
| 2,504,142 | 4/1950 | Mingea | 165/46 |
| 3,148,957 | 9/1964 | Ballard | 34/99 X |
| 4,172,495 | 10/1979 | Zebehr et al. | 128/400 X |
| 4,425,916 | 1/1984 | Bowen | 128/403 |

FOREIGN PATENT DOCUMENTS

| | | | |
|---|---|---|---|
| WO82/04184 | 12/1982 | PCT Int'l Appl. | 128/400 |
| 17621 | 9/1898 | Switzerland | 165/46 |
| 5312 | of 1880 | United Kingdom | 165/46 |

*Primary Examiner*—Anton O. Oechsle
*Attorney, Agent, or Firm*—Neal J. Mosely

[57] ABSTRACT

An improved scalp cover is provided for the circulation of liquid coolant to reduce and control scalp temperature during chemotherapy. Device consists of series of tubes adjustably positioned about the scalp to maintain a uniform and controlled scalp temperature. Use of a series of tubes provides more accurate temperature control and reduces temperature drop in the circulating liquid coolant.

2 Claims, 2 Drawing Figures

SKIN TEMPERATURE CONTROL

TECHNICAL FIELD

This invention pertains to a device for controlling the temperature of the skin of the human body. More particularly, this invention pertains to a scalp cover useful in scalp hypothermia permitting the use of a liquid coolant circulating system to prevent hair loss (alopecia) during chemotherapy.

BACKGROUND OF THE INVENTION

Many cytotoxic agents used in cancer chemotherapy cause a rapid and sometimes complete loss of hair. The development of hair loss is a traumatic experience, though not a dangerous side effect of cancer treatment. In addition to the inherent psychological stress of chemotherapy, hair loss may increase the despair of the patient to the point of social withdrawal. Scalp cooling during chemotherapy can alleviate hair loss by reducing metabolic activity in the scalp.

Several types of caps containing ice or other liquids are widely used to effect scalp cooling during chemotherapy. These caps have shown a degree of effectiveness but have several drawbacks. Specifically, such caps provide no control over the cooling process, are unduly heavy, are uncomfortable because of the length of time in use, frequently are not reusable and, at times, have a traumatic effect on the patient as a result of the intense cold.

Clothing incorporating a circulating liquid coolant system is a development of recent years. Much work in this area has been done by the National Aeronautics and Space Administration (NASA) for the purpose of providing the necessary protective clothing during space missions. This type of clothing has generally employed a fabric with a network of tubing attached thereto through which is circulated a liquid coolant or heat exchange fluid. The tubing was somewhat randomly affixed to such fabric as the purpose was to provide a somewhat general overall body temperature control as distinguished from a fixed, precise temperature control at a particular part of the body. While such temperature controllable fabrics have proven adequate for their intended purpose, they have not proved to be totally satisfactory from the standpoint of scalp hypothermia. The ramdom positioning of circulating tubes makes precise temperature control exceedingly difficult, if not impossible. The nature of the construction of these composite fabrics is such that little adjustment capabilities are present and, as a result, any particular garment must be tailor made to fit the particular body size involved.

It is an object of this invention to provide an improved scalp cover useful in scalp hypothermia and employing a liquid coolant circulating system to prevent hair loss during chemotherapy.

It is another object of this invention to provide such an improved scalp cover that is readily adjustable to fit any particular patient's head size.

It is another object of this invention to provide such an improved scalp cover providing very precise temperature control to the entire scalp.

Other objects of this invention will become apparent from the description contained herein.

STATEMENT OF THE INVENTION

The novel scalp cover of this invention comprises a series of individual, flexible, elastomeric tubes positioned horizontally on top of and around the scalp in a close, spaced apart relationship with regard to each other and in as close a relationship with the skin as permitted by the hair of the scalp. Each tube on the top of the head is positioned in a horizontal spiral. Each tube about the side of the head is of a length such that it will circle the scalp twice and provide an intermediate adjusting loop extending from and free of the back of the scalp. The tubes are maintained in place by flexible, elastomeric retainer strips positioned at the front, top and each side of the scalp cover. These flexible retainer strips facilitate adjusting the scalp cover to any particular head size. One end of all of the tubes is attached to a manifold providing an inlet for an incoming liquid coolant. The other end of all of the tubes is attached to a manifold for the outflow of the liquid coolant. The end portions of the tubes positioned around the scalp and the corresponding adjusting loop are attached to a flexible, elastomeric retainer. This configuration permits adjusting and maintaining the circumferential dimension of the tubes around the scalp to accomodate varying scalp sizes. By utilizing a series of tubes to cover the scalp, instead of one continuous tube, adjustment of the scalp cover is facilitated and a minimum temperature drop in the coolant is obtained.

DESCRIPTION OF THE PREFERRED EMBODIMENT

Figure 2:
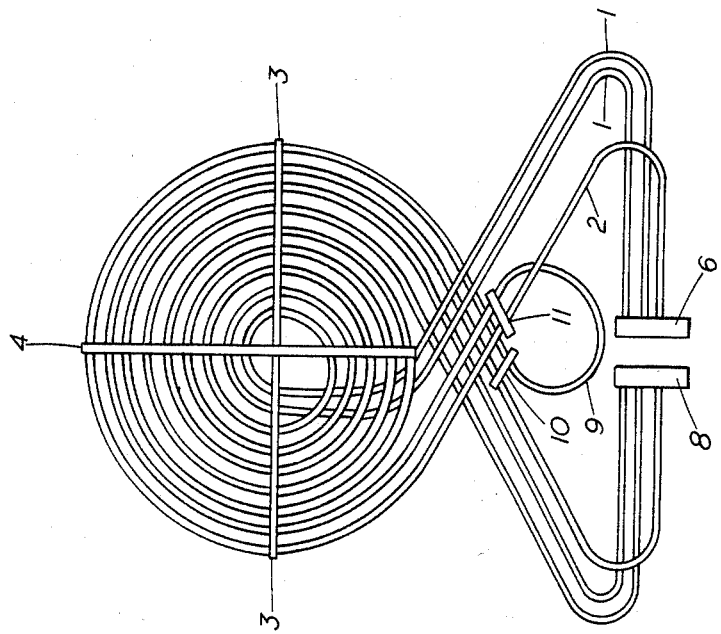
FIG. 2 is a representation of the top view of the scalp cover depicting the configuration of the tubes as positioned on the top and around the scalp. Each tube is represented by a single solid line.
Figure 1:
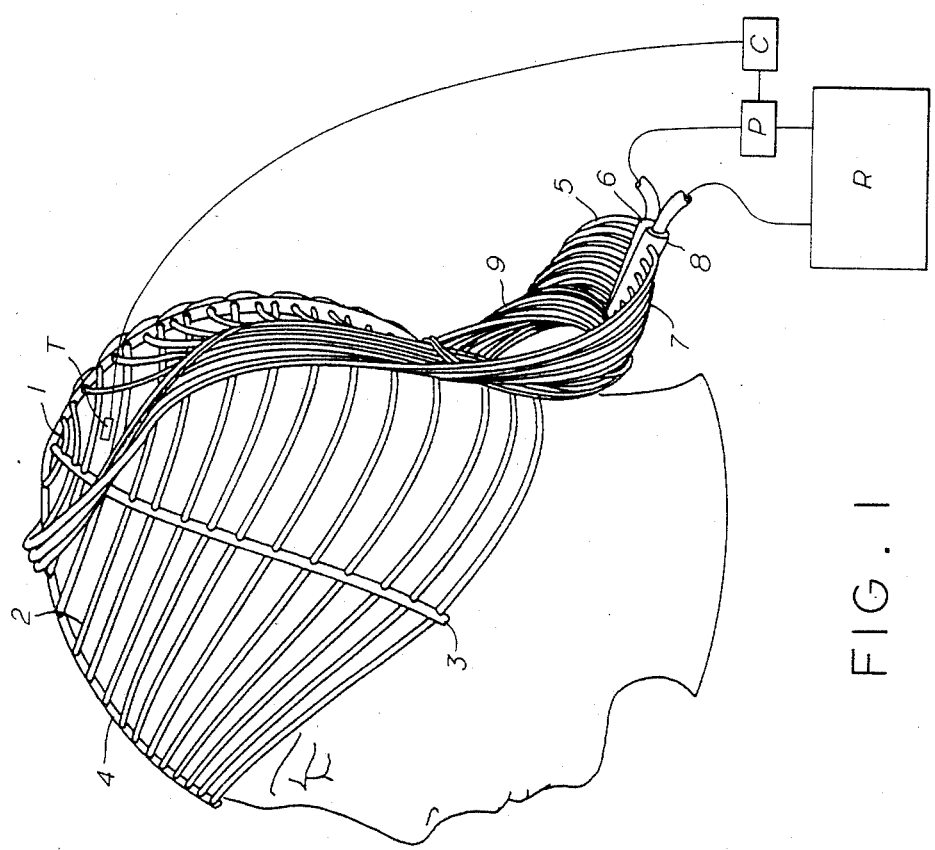
FIG. 1 is a schematic side view of the scalp cover as positioned on the head.

Referring to both FIGS. 1 and 2, the scalp cover of this invention is made up of top tubes 1 spirally positioned on the top of the scalp and tubes 2 positioned about the head. All such tubes are positioned in a close, spaced apart relationship with each other to form loops. The tubes employed had an internal diameter of approximately $\frac{1}{8}$ inch and an external diameter of approximately 3/16 inch and were fabricated from plasticized polyvinyl chloride, marketed under the registered trademark "Tygon." The tubes were retained in place by retainers 3 and 4. The retainers were also tubes of flexible, elastomeric material having an inside diameter of approximately 3/16 of an inch and an outside diameter of approximately $\frac{1}{4}$ of an inch. The tubes on top of and about the head passed through holes punched into retainers 3 and 4, the holes being of such a size to permit passage of the tubes and retention of the position of the tube once properly positioned.

Each tube 2 about the head was of such a length to circle the head twice and provide intermediate adjusting loop 9.

One end 5 of all the tube 1, 2 were connected to manifold 6 which provided an inlet for the liquid coolant. The other end 7 of all the loops were attached to manifold 8 providing an outlet for the liquid coolant.

The ends of the loops formed by tube 2 about the head and the intermediate loops 9 were attached to retainers 10 and 11. Intermediate loop 9 and the length of the ends of the tubes 2 about the head, provided adjustment means for the circumferential dimension of the scalp cover.

In actual operation, a sanitary paper scalp cover was first affixed to the patient's head. The scalp cover of this invention was then placed on top of the paper cover. A stretchable cap of knitted polyester was then placed on top of the scalp cover of this invention to help maintain it in position and as close to the scalp as possible.

The coolant reservoir R was a container well insulated with polyurethane foam, having a capacity of approximately two gallons. The reservoir R was filled with water and ice, the mixture having a temperature of approximately 33° F.

Attached to the reservoir R was a two speed pump P, operating on 8–16 volts DC. A flexible tube connected the pump P to the inlet manifold of the scalp cover and another flexible tube was connected to the outlet manifold of the scalp cover to return circulating liquid coolant back to the reservoir R.

A thermistor T was attached to the top of the scalp of the patient and to a control unit C which activated the pump P. The thermistor T was calibrated to maintain a scalp temperature of 69° F., activating the pump to circulate liquid coolant when the temperature of the scalp exceeded 69° F. and to inactivate the pump P when the temperature of the scalp fell below 69° F. Constant control of the scalp temperature was found to be exceptionally precise. The use of multiple tubes resulted in an exceptionally low temperature differential between the inlet and outlet. A temperature drop of only from 1°–2° F. was observed. Precooling of the scalp to 69° F. prior to initiation of chemotherapy was accomplished in 10–20 minutes. Initial wetting of the hair, prior to affixing the scalp cover of this invention, which prewetting of the hair has been found necessary when using some of the prior art devices, did not prove to be necessary when employing the instant invention. Furthermore, the amount of hair on the scalp appeared to have no real measurable effect on the ability to attain and maintain a predetermined scalp temperature when employing the scalp cover of this invention.

While the scalp cover of this invention has been described in connection with its use in preventing alopecia during chemotherapy, it's application is not so limited. For example, scalp cooling is commonly employed by race car drivers during races. The scalp cover of this invention would be equally applicable in such applications. Other therapeutic uses of the scalp cover of this invention can be readily visualized.

What is claimed is:

1. A scalp cover for controlling scalp temperature by means of a liquid coolant circulating within said scalp cover comprising a series of individual, flexible, elastomeric tubes positioned horizontally on top of and around the scalp in a close, spaced apart relationship with regard to each other and in as close a relationship with the skin as permitted by the hair of the scalp, each tube around the scalp being of a length such that it will circle the scalp twice with an intermediate adjusting loop extending from and free of the back of the scalp; each tube on top of the scalp being positioned in a horizontal spiral; one end of all of said tubes being attached to a manifold providing an inlet for incoming liquid coolant and the other end of all of said tubes being attached to a manifold for the outflow of said liquid coolant; said tubes affixed to flexible elastomeric retainer strips positioned at the front, top and each side of the scalp cover to maintain a variable, spaced apart, relationship of the tubes to accomodate varying scalp sizes; the end portions of each tube positioned around the scalp and the corresponding adjusting loop being affixed to a flexible elastomeric retainer at the back of the scalp cover permitting adjusting and maintaining the circumferential dimension of the tubes around the scalp to accomodate varying scalp sizes.

2. The scalp cover of claim 1 including, in combination therewith, a reservoir of liquid coolant, means for circulating said liquid coolant through the tubes of said scalp cover, means for measuring scalp temperature and means for controlling flow of liquid coolant based on scalp temperature.

* * * * *